US00PP09449P

United States Patent [19]

Lamb

[11] Patent Number: Plant 9,449

[45] Date of Patent: Feb. 6, 1996

[54] ANTHURIUM PLANT NAMED 'LAVENDER ARISTOCRAT'

[75] Inventor: Ann E. Lamb, Sebring, Fla.

[73] Assignee: Twyford International, Inc., Sebring, Fla.

[21] Appl. No.: 366,330

[22] Filed: Dec. 29, 1994

[51] Int. Cl.[6] ..... A01H 5/00

[52] U.S. Cl. ..... Plt./88.1

[58] Field of Search ..... Plt./88.1

*Primary Examiner*—James R. Feyrer
*Attorney, Agent, or Firm*—Foley & Lardner

[57] ABSTRACT

An Anthurium plant named Lavender Aristocrat having lavender spathes with pale lavender spadix, and durable dark green shining leaves. The spathes change color as they age to cream spotted with green.

1 Drawing Sheet

The present invention comprises a new and distinct cultivar of Anthurium, botanically known as *Anthurium hybrida*, and referred to by the cultivar name Lavender Aristocrat.

The new cultivar is a mutation discovered among tissue culture derived plants of Pink Aristocrat, disclosed in U.S. Plant Pat. No. 7,441. Lavender Aristocrat was discovered by the inventor, Ann E. Lamb, in Apopka, Fla. in June 1992. The new cultivar was distinguished by its lavender spathes and pale lavender spadix. The new cultivar was first asexually reproduced by division under the supervision of the inventor in August 1992 in Apopka, Fla., and such propagation, and subsequent propagations, have demonstrated the stability of the combination of characteristics of Lavender Aristocrat from generation to generation.

The following observations, measurements and values describe plants grown in Apopka, Fla. under shadehouse conditions which closely approximate those generally used in horticultural practice.

The following traits have been repeatedly observed to be characteristics which in combination distinguish Lavender Aristocrat from other cultivars, particularly parent cultivar Pink Aristocrat to which comparative reference is made.

1. The plant produces lavender spathes with a pale lavender spadix. By contrast, the spathe color of Pink Aristocrat is a deep pink (50B) and the spadix a lighter pink (54D).

2. The spathes change as they age from lavender to cream spotted with green, and finally to green. The duration of color is approximately the same as Pink Aristocrat, although the lavender mature color does not remain as long as the pink mature color of Pink Aristocrat's spathes.

3. The flowers are held well above the leaf canopy.

4. On a mature plant, the axillary shoots can bloom from the first expanded leaf.

5. The leaves are dark green, have good texture and a shiny surface, and are durable.

6. The plant is free branching.

All color references are measured against The Royal Horticultural Society Colour Chart. Colors are approximate as color depends on horticultural practices such as light level and fertilization rate, among others, without, however any variance in genotype.

The color photographic drawing comprises a top perspective view of the inflorescence and foliage of a plant of Lavender Aristocrat in a 15 cm pot approximately 52 weeks after planting a 20-week-old liner obtained by tissue culture and grown under appropriate growing conditions. Colors are as accurate as possible with color illustrations of this type.

Origin: Mutation from Pink Aristocrat.

Classification: *Anthurium hybrida*, cv., Lavender Aristocrat.

Propagation: Asexual production either by tissue culture or division.

Plant: In a 15 cm pot for a plant grown from a 20-week-old liner after 52 weeks under appropriate growing conditions, Lavender Aristocrat reaches a mature size of approximately 32 cm to 47 cm in height and approximately 52 cm to 64 cm in width.

Leaves:

*Form.*—The leaf blade is ovate with an acuminate tip and a truncate base. The margins are entire. The midrib tends to curve downward over the length of the leaf. The leaf blade tends to be straight over the width of the leaf.

*Size.*—Leaf blades of a mature-sized plant are approximately 20.5 cm to 22.5 cm in length and approximately 8.5 cm to 11.2 cm in width.

*Petiole.*—The petiole is approximately 19 cm to 21.5 cm in height from the base of the petiole to the base of the leaf blade on the primary shoot. Secondary shoots are somewhat smaller depending on the age of the shoot. The petiole is approximately 3.5 mm in diameter just below the geniculum. The petiole below the geniculum is straight or slightly curved.

*Petiole wings.*—Petiole wings are approximately 21 mm to 24 mm in length and approximately 4 mm to 5 mm in width at their midpoint. The tip of the petiole wings is emarginate. There is approximately 12.3 cm to 14.5 cm between the top of the wing and the base of the geniculum.

*Geniculum.*—The geniculum is approximately 30 mm to 33 mm in length, approximately 4 mm in diameter, and is often curved. The color is 145A. There is no space between the top of the geniculum and the base of the leaf blade. The geniculum is prominent.

*Veins.*—Veins are sunken, with the leaf blade being slightly convex between veins on the upper surface. The midrib protrudes from the upper surface of the leaf for approximately ⅔ the length of the leaf. Well-defined primary veins on leaves radiate out from the juncture of the petiole and the leaf. Veins and midrib stand out prominently on the lower side. There are approximately six (6) primary veins on the leaf.

*Lobes.*—The leaf has two (2) lobes extending past the petiole. The distance from the petiole/leaf juncture to the highest point on the lobes is approximately 4 cm to 4.5 cm.

*Color.*—Upper surface: Darker and greener than, but closest to 137A. Lower surface: 146C. Midrib, upper surface: 144A. Midrib, lower surface: 145C. Petiole: 144A. Petiole wing: 144A–B.

Inflorences (spathe):

*Immature.*—The spathe is tightly rolled around the spadix and extrudes from the petiole sheath. The spathe is fully open approximately when the pedicel is fully elongated, about 43 cm to 47 cm above the soil surface. The color of the pedicel is darker and greener than, but closest to 145A.

*Mature.*—Size: The flattened spathe is approximately 7.1 cm to 8.9 cm long and approximately 5.1 cm to 6 cm in width. Color: Fully Open (upper surface): 77C–D. Fully Open (lower surface): 77D. Faded (upper and lower surfaces: 158C–D, often with spots of green. Arrangement: The spathe stands up on straight wiry pedicels and opens vertically above the leaves. Shape: The spathe is ovate with a cuspidate apice that is straight. The tip of the spathe is often curled downward. It is cupped when first open and approximately 6.4 cm to 7.8 cm in length, 4.8 cm to 5.5 cm in width, and 11 mm in depth. The spathe flattens slightly and may reflex slightly as it ages. Flowering Time: After approximately 12 months from a 20-week-old liner for an untreated plant, as shown in the photographic drawing and depending on season, approximately 8 to 10 blossoms are present. Smaller blossoms may occur on less mature growth. Approximately 1–3 flowers are present about 6 months after planting a 20-week-old liner.

Reproductive organs:

*Spadix.*—Size: Approximately 2.8 cm to 3.7 cm in height and approximately 6 mm in width. Color: When the spathe unrolls, the spadix gradually changes to 145A and 158A before senescing. Stamens: Anthers and filaments are not clearly visible. Pollen: White in color. Pistil: Lighter than 155D in color, protruding between the staminate flowers, firmly fixed to the main axil. The pistilate flowers extend approximately 0.2 mm beyond the staminate flowers.

Roots: White fleshy roots with fine laterals. Roots initiated above the soil have a pink cast.

It is claimed:

1. A new and distinct cultivar of Anthurium plant named Lavender Aristocrat, as illustrated and described.

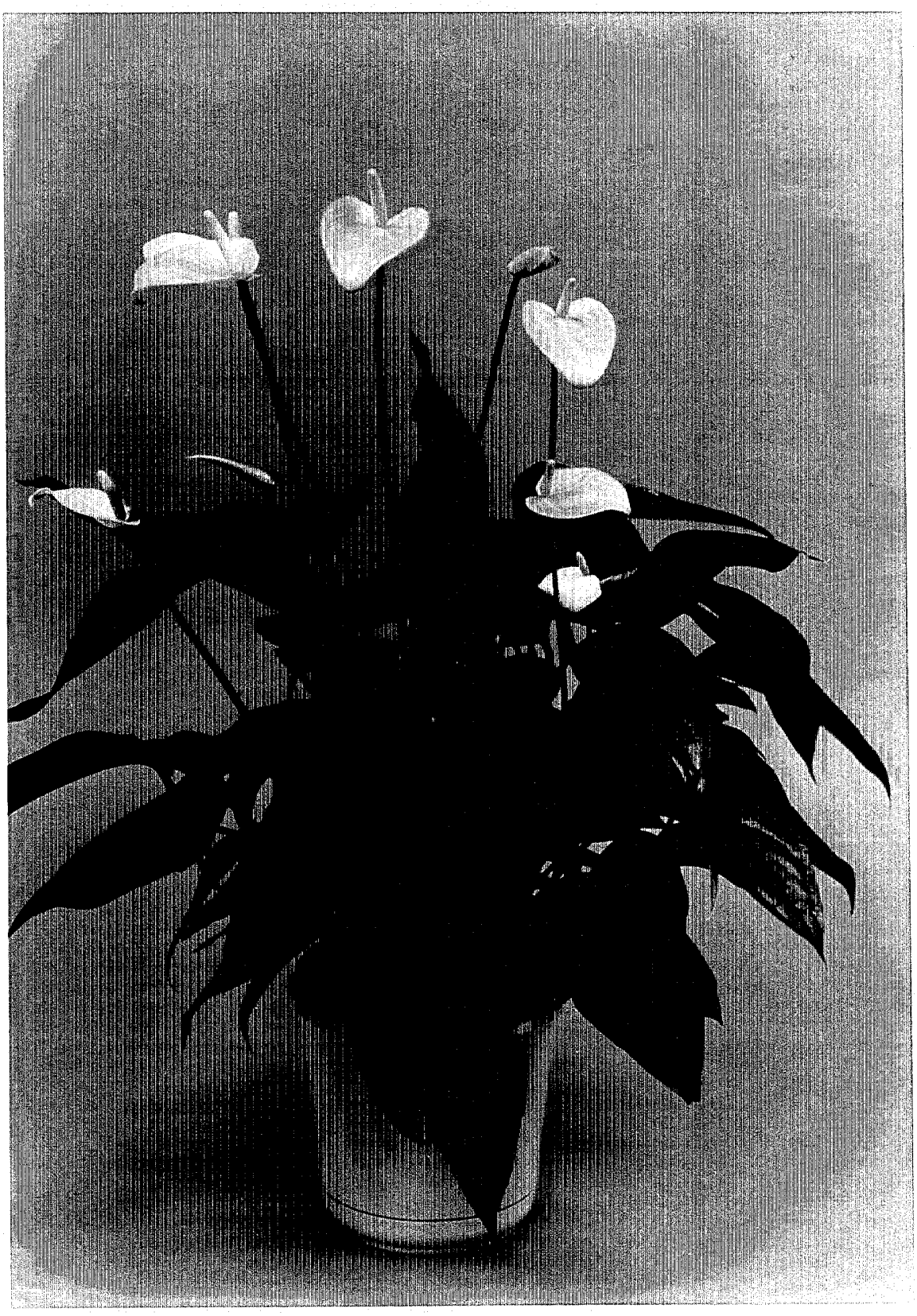

* * * * *